(12) United States Patent
Block et al.

(10) Patent No.: US 6,196,649 B1
(45) Date of Patent: Mar. 6, 2001

(54) CONVERTIBLE SURGICAL EQUIPMENT AND APPLIANCE SUPPORT SYSTEM

(75) Inventors: Roland D. Block, Painesville, OH (US); Robert J. Byrd, Marbury, AL (US); Mark E. Chiffon, Erie, PA (US); John D. Marshall, Montgomery, AL (US)

(73) Assignee: Steris Corporation, Mentor, OH (US)

( * ) Notice: Subject to any disclaimer, the term of this patent is extended or adjusted under 35 U.S.C. 154(b) by 0 days.

(21) Appl. No.: 09/232,300

(22) Filed: Jan. 15, 1999

Related U.S. Application Data
(60) Provisional application No. 60/071,536, filed on Jan. 15, 1998.

(51) Int. Cl.$^7$ .................................................. A47B 81/00
(52) U.S. Cl. ............................... 312/209; 312/205; 5/658
(58) Field of Search ..................................... 312/209, 107, 312/108, 111, 223.1, 223.6, 246, 265.1, 265.3, 265.6, 205; 5/600, 658, 503.1; 248/323, 324, 326, 327, 122.1

(56) References Cited

U.S. PATENT DOCUMENTS

| | | | |
|---|---|---|---|
| 3,329,473 | * 7/1967 | Dickson | 312/108 |
| 3,435,575 | * 4/1969 | Pottiez | 312/108 |
| 4,452,499 | * 6/1984 | Verburg | 312/209 |
| 4,475,322 | * 10/1984 | Russo et al. | 312/209 X |
| 4,795,122 | 1/1989 | Petre | 248/317 |
| 4,993,683 | * 2/1991 | Kreuzer | 248/327 X |
| 5,026,017 | 6/1991 | Kreuzer | 248/324 |
| 5,072,906 | * 12/1991 | Foster | 5/658 X |
| 5,108,064 | 4/1992 | Kreuzer | 248/327 |
| 5,186,337 | * 2/1993 | Foster et al. | 5/658 X |
| 5,291,838 | * 3/1994 | Ferchau et al. | 312/223.6 X |
| 5,299,338 | * 4/1994 | Foster | 5/658 |
| 5,470,139 | * 11/1995 | Hsiao | 312/265.1 X |
| 5,490,652 | * 2/1996 | Martin | 248/282.1 |
| 5,537,289 | * 7/1996 | Dahl | 312/209 X |
| 5,618,090 | * 4/1997 | Montague et al. | 312/246 X |
| 5,695,263 | * 12/1997 | Simon et al. | 312/265.1 X |
| 5,975,660 | * 11/1999 | Tisbo et al. | 312/108 X |

FOREIGN PATENT DOCUMENTS

| | | | |
|---|---|---|---|
| 3034013 | * | 4/1982 | (DE) . |
| 9308400 | | 9/1993 | (DE) . |
| 2645007 | * | 10/1990 | (FR) . |
| 2082893 | * | 3/1982 | (GB) . |
| 2083878 | * | 3/1982 | (GB) . |
| 2133973 | | 8/1984 | (GB) . |

* cited by examiner

*Primary Examiner*—James O. Hansen
(74) *Attorney, Agent, or Firm*—Fay, Sharpe, Fagan, Minnich & McKee, LLP

(57) ABSTRACT

A convertible medical appliance support apparatus includes a box-shaped hollow main body portion A suspended from overhead by a support apparatus B. A horizontal support table C extends forward from the front face of the vertical main body column to form a platform for supporting associated medical equipment. Multiple gas connections D are provided the main body portion together with a manual handle E near the bottom of the main column on a side of the column opposite from the support table to provide a convenient point to grip and move the body column into a desired position. Manually actuatable controls are provided at the handle, including brake release pushbuttons I and a motorized height adjustment toggle switch J. Multiple electrical connections F are included on the main body together with optional shelves G selectively attachable below the main platform. The appliance support system is convertible through use of replaceable pairs of face wall members that are held in a vertical orientation by a set of elongate corner connection members adapted to selectively engage and attach to edges of the face wall members. The hollow main body portion is easily re-configurable in width, depth, and height dimensions by mere replacement of selected pairs of face wall or corner members to realize a medical appliance support column having a range of selectable sizes and cross-sectional areas H.

12 Claims, 11 Drawing Sheets

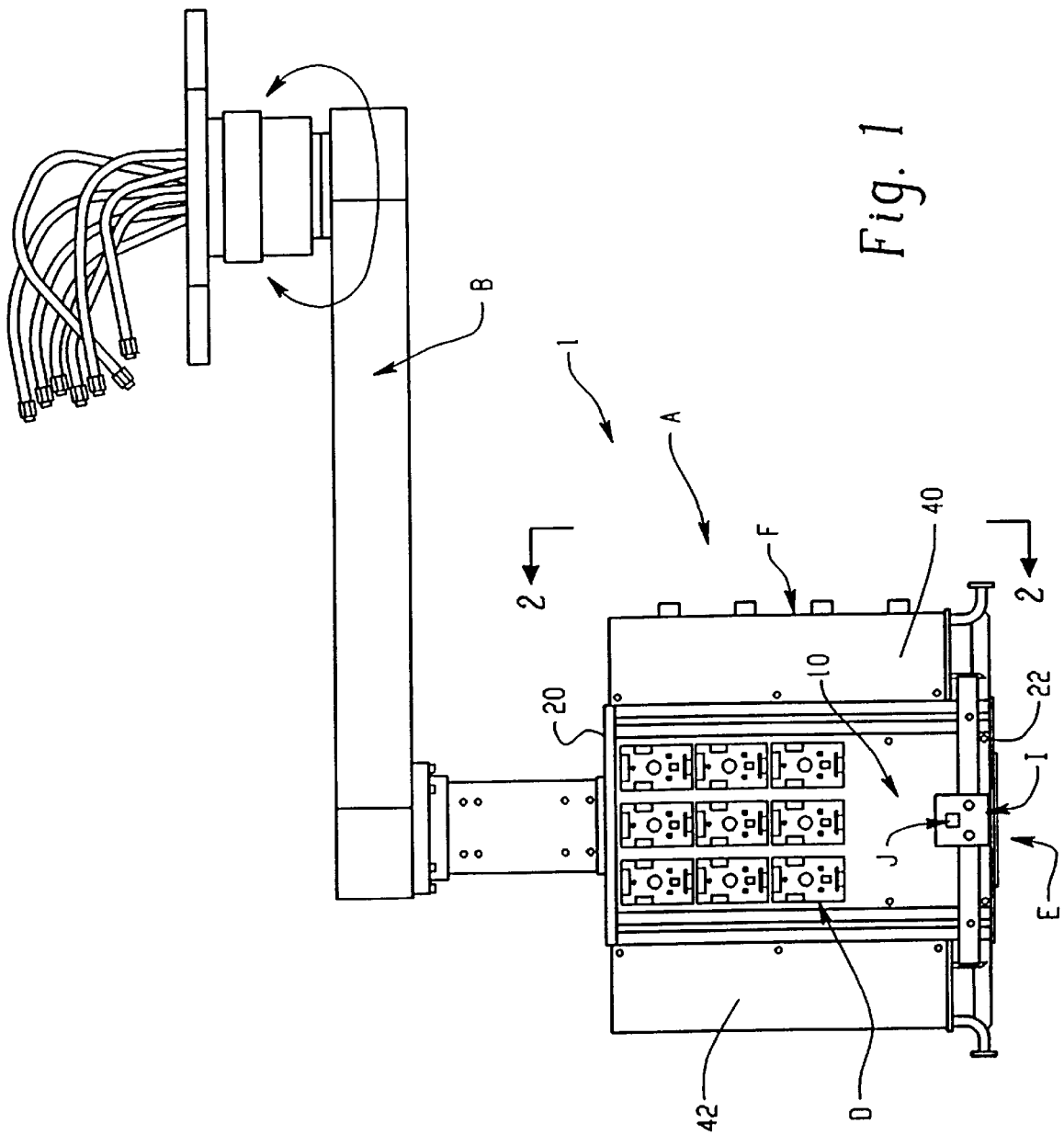

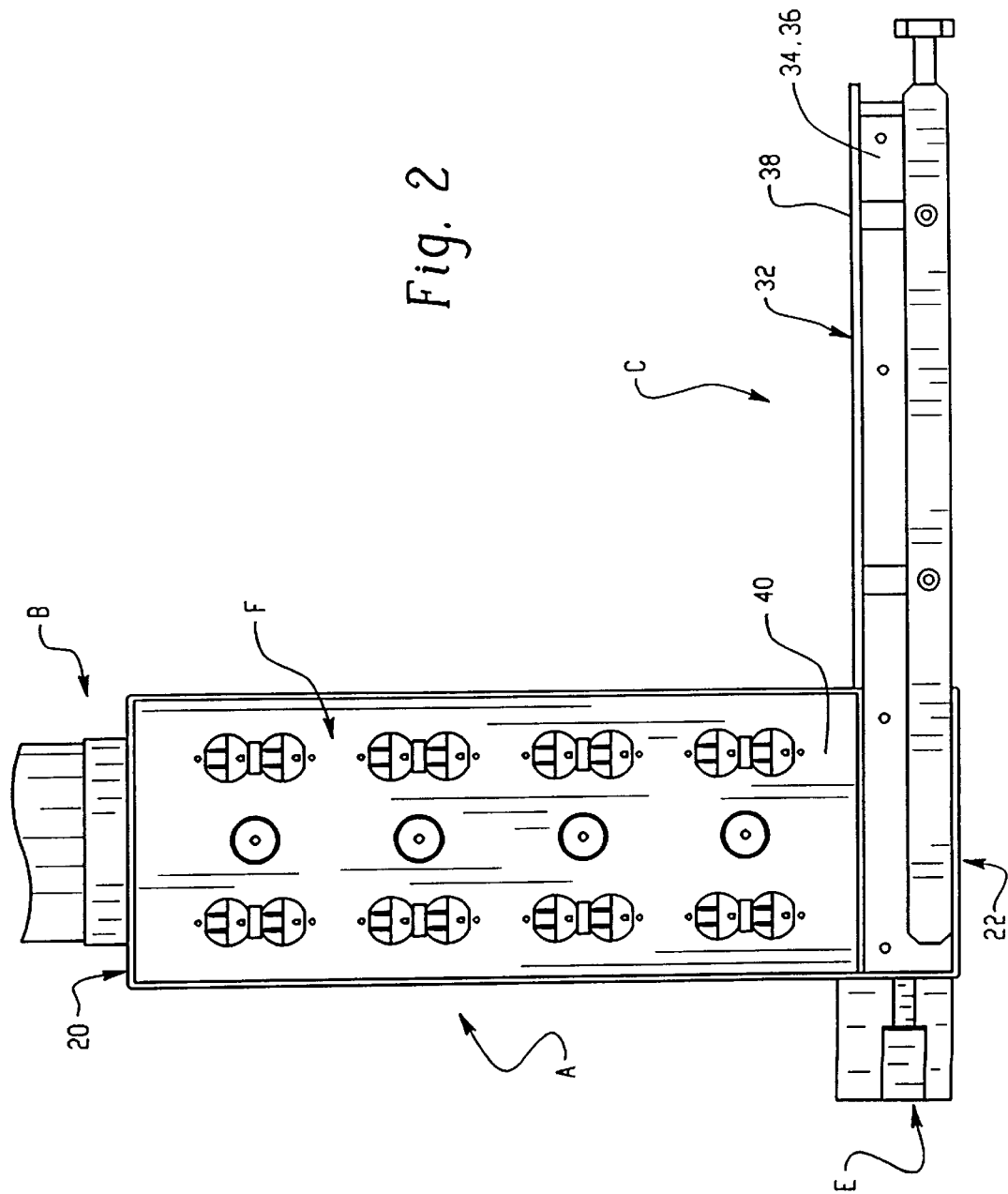

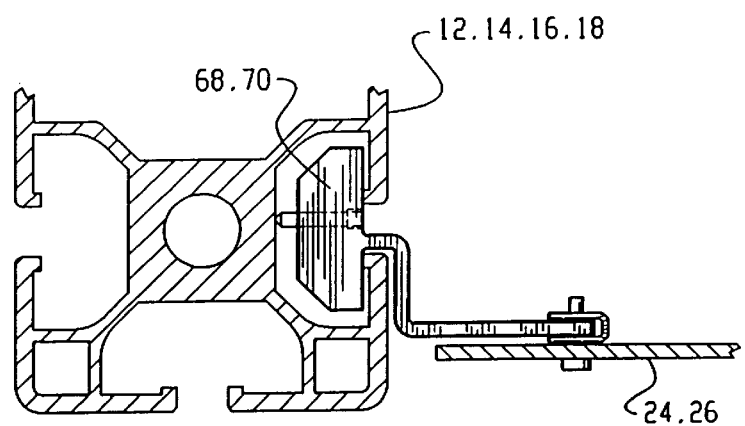
Fig. 11
Fig. 10

CONVERTIBLE SURGICAL EQUIPMENT AND APPLIANCE SUPPORT SYSTEM

CROSS-REFERENCE TO RELATED APPLICATION

This application claims the benefit of U.S. Provisional Application No. 60/071,536, filed Jan. 15, 1998.

BACKGROUND OF THE INVENTION

The present invention relates to overhead medical appliance support apparatus, and, more particularly, to an improved ceiling-mounted surgical equipment management system. The invention is particularly applicable for use in operating rooms during surgical procedures or the like and will be described with reference thereto. However, it is to be understood that the present invention is useful in a variety of situations, environments, and applications wherever overhead support for electrical, pneumatic, or other equipment is needed including non-medical uses and environments such as industrial and commercial applications.

U.S. Pat. Nos. 5,026,017 and 5,108,064 to Kreuzer teach a medical appliance support apparatus particularly adapted for use in intensive care stations of hospitals. The appliance support apparatus device taught there includes a generally rectangular support column suspended from overhead by a ceiling-mounted support arm. The support column is constructed from two mutually parallel profiled wall members, each being formed integrally and each having at least one longitudinally extending groove formed therein. A pair of thin wall members extend transversely to the profiled members for interconnecting the profiled members such that together, the wall members and the profiled members define an inner supply channel. One or more slidable support members are disposed in the longitudinal grooves provided in the profiled members for suspending medical or surgical equipment therefrom.

Although medical appliance support equipment such as taught by the above Kreuzer patents are useful to a limited degree, they are somewhat constrained in versatility and are oftentimes inconvenient to use. As an example, the Kreuzer appliance support apparatus does not provide multiple gas outlet connections. In addition, in order to maneuver the Kreuzer appliance support into a usable position, the circulating nurses or other medical staff most often position their bodies between the support system and the surgical field in order to pull the support system towards the surgical field. This practice, as those skilled in the art would appreciate, is prone to compromise the surgical field.

In addition to the above problems associated with the prior appliance support apparatus of the type taught in the Kreuzer patents, the inability to mechanically expand or upgrade the system to include additional support members, such as by extending the support column vertically to accommodate additional shelves or support brackets or the like, has proved to be costly and somewhat limiting.

Further, the construction taught in the Kreuzer patents does not lend itself for ready expansion of the inner supply channel because the two mutually parallel profiled wall members are each formed integrally. In that regard, the pair of profiled members extend uninterrupted from the front face of the support column to the rear face precluding the use of intervening removable wall portions. Therefore, only the width of the Kreuzer appliance support column can be modified. The depth of the column cannot be changed.

Accordingly, it would be desirable to provide a surgical equipment management system of the type which includes operator controls with a manual handle and electric motor and/or brake controls, or the like, provided near the rear face of the support column opposite from the medical equipment adjacent the surgical field. With the controls conveniently located on the back side of the column, circulating nurses or other interventionists need not worry about contaminating the surgical field through accidental missteps or mishandling while maneuvering the surgical management system into place.

It would further be desirable to provide a surgical equipment management system including a plurality of gas connection outlets on the back side of the vertical main body column for ease of access. The multiple gas connections would preferably include redundant gas connections which may from time to time prove useful as backup gas supplies during certain emergency situations.

Still further, it would be desirable to provide a surgical equipment management system of the type which is readily expandable in main column cross-section to accommodate a larger quantity of electrical and/or gas lines, connections or the like. The surgical equipment management system would preferably also be vertically extendable to include additional lower shelf portions for supporting additional or secondary medical equipment thereon. Preferably, the vertical extension would simply require the attachment of additional extension members to the bottom of the main body column. For width and depth expansion of the main body column, the improved surgical equipment management system would preferably include a set of four vertical elongate support members disposed in the four corners of the main body column with a corresponding set of four face panels disposed therebetween. In that way, both width and depth adjustment of the main body column is enabled by simply substituting opposed face panels with second opposed face panels of different size.

SUMMARY OF THE INVENTION

Accordingly, the present invention is a surgical equipment management system with a manual handle and operator controls for electric motor and/or brake operation, or the like, provided at the rear face of the support column on a side opposite from the surgical field. In that way, circulating nurses or other interventionists need not worry about contaminating the surgical field through accidental missteps or mishandling while maneuvering the surgical management system of the instant invention into place.

Further, the surgical equipment management system of the instant invention includes a plurality of gas connection outlets on the back side of the vertical main body column. The gas outlets are arranged in three rows and three columns for ease of access. The multiple gas connections include redundant gas connections for use as backup gas supplies as necessary during certain emergency situations.

Still further, the main column of the surgical equipment management system of the invention is readily expandable to accommodate a larger quantity of electrical and/or gas lines, connections, or the like. Adjustment of the width of the column is also useful to provide appliance support shelves of various widths. Adjustment of the depth of the column is useful as well to control the torque moment experienced by the shelf support arms.

For width and depth expansion of the main body column, the improved surgical equipment management system includes a construction formed by a set of four vertical elongate support members disposed in the four corners of the main body column connected to a corresponding set of four face panels disposed therebetween. In that way, both width and depth adjustments of the main body column are accomplished simply by substituting opposed face panels with second opposed face panels having a desired different width.

The surgical equipment management system is also vertically extendable to include additional lower shelf portions for supporting additional or secondary medical equipment thereon. The vertical extension simply requires the attachment of additional extension members to the bottom of the main body column.

Therefore, in accordance with the present invention, an improved surgical equipment management system is provided including an upper substantially rectangular closure member adapted to connect the management system to an operatively associated ceiling mount member, a lower substantially rectangular closure member, and a first pair of elongate corner support members extending substantially vertically between the top closure member and the bottom closure member. In addition, a second pair of elongate corner support members are provided extending substantially vertically between the top closure member and the bottom closure member in a spaced apart parallel relationship with the first pair of elongate corner support members. A first pair of face wall members extend transversely between the first and second pairs of corner support members to form opposed front and rear face panels of the support column. A first pair of side wall members are connected between the first and second pairs of elongate corner support members to provide left and right side face panels. Collectively, the elongate corner support members and the first pair of face and side wall members define a substantially cylindrical main body column portion of the surgical equipment management system. The main body column has a rectangular transverse cross-section. A medical appliance support member is connected to at least one of the first and second pair of elongate corner support members. The medical appliance support member is adapted to support an operatively associated medical appliance on the surgical equipment management system. Lastly, a manual handle with manually actuatable operator controls is connected to the main body column on a side opposite the medical appliance support member.

It is an advantage of the present invention that the manual handle and operator controls for electric motor and/or brake operation are provided at the rear face of the support column opposite from the side of the column that faces the surgical field. This enables movement of the device into the desired location without compromising the sterile surgical field.

It is a further advantage of the present invention that a plurality of gas connection outlets are provided on the back side of the vertical main body column arranged in a regular array of rows and columns, preferably three rows and three columns, for ease of access. The multiple gas connections arranged in that manner occupy minimal space and preferably include several redundant gas connections for use as auxiliary backup gas supplies as necessary during certain emergency situations.

A still further advantage of the invention is that the appliance support system is readily adjustable in main column cross-section to accommodate large and small quantities of electrical and/or gas lines, connections or the like. The invention is also vertically extendable to include additional lower shelf portions for supporting additional or secondary medical equipment thereon. The vertical extension simply requires the attachment of additional extension members to the bottom of the main body column. For width and depth expansion of the main body column, the improved surgical equipment management system includes a construction formed by a set of four spaced apart vertical elongate support members disposed in the four corners of the main body column. The vertical members are connected to a corresponding set of four face panels disposed therebetween. In that way, both width and depth adjustments of the main body column are enabled simply by substituting sets of opposed face panels with replacement sets of opposed face panels having a desired different width.

Still other advantages and benefits of the invention will become apparent to those skilled in the art upon a reading and understanding of the following detailed description.

BRIEF DESCRIPTION OF THE DRAWINGS

The invention may take form in various parts and components and arrangements of parts and components, and in various steps and arrangements of steps. The drawings are only for purposes of illustrating a preferred embodiment and are not to be construed as limiting the invention.

FIG. 1 is a rear elevational view of the subject surgical equipment management system formed in accordance with the present invention carried by an overhead single arm suspension system illustrating the gas connection panel, the manual handle and motor/brake control, and the left and right electrical boxes;

FIG. 2 is a side elevational view of the surgical equipment management system of FIG. 1 as viewed from the left side thereof, relative to the front face, illustrating the left electrical connection box;

DETAILED DESCRIPTION OF THE PREFERRED EMBODIMENT

Figure 1A:
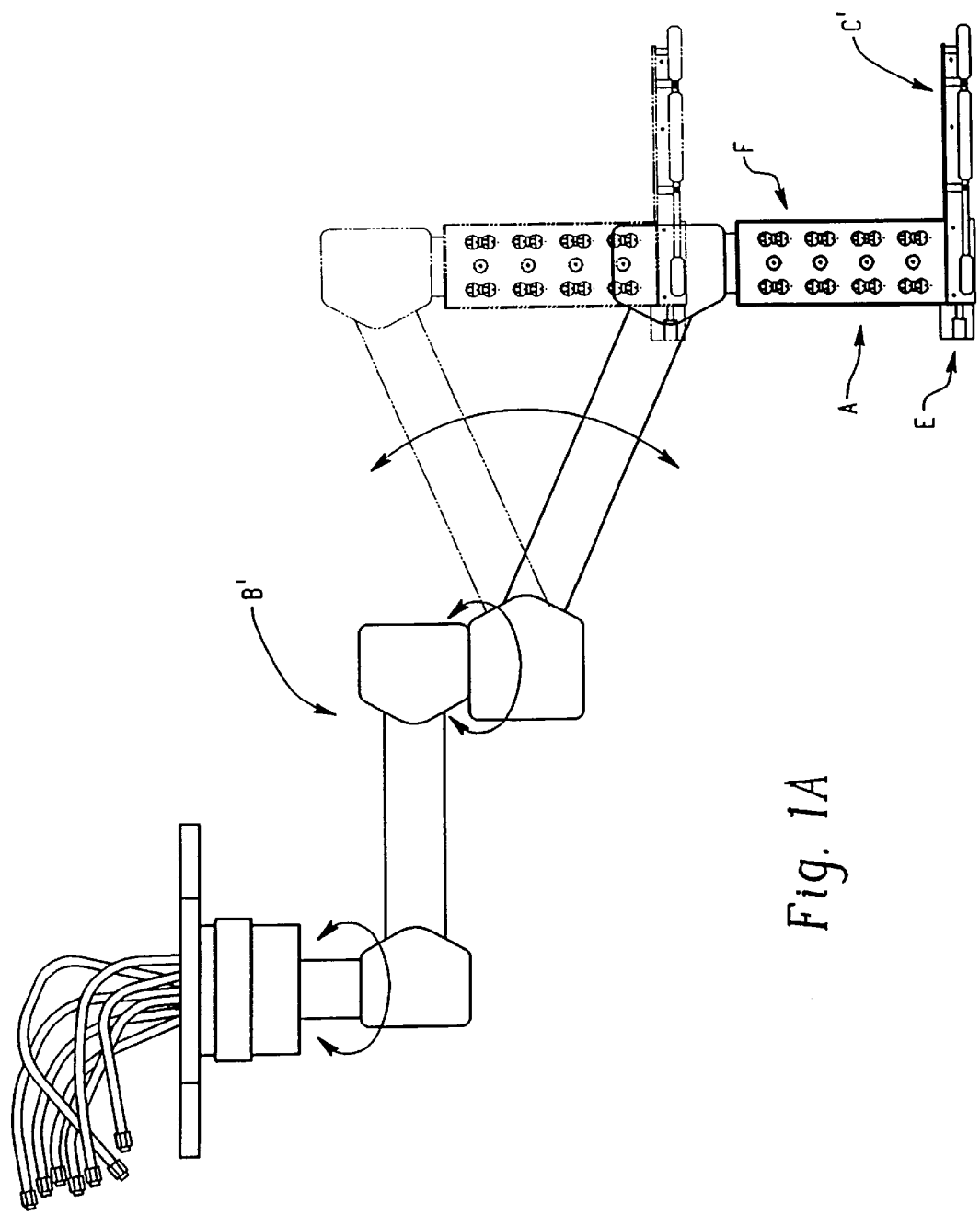
FIG. 1A is a side elevational view of the subject surgical equipment management system formed in accordance with the present invention carried by an overhead double arm suspension system illustrating the medical appliance support shelf, the right electrical boxes and the manual handle and motor/brake control.
Figure 3:
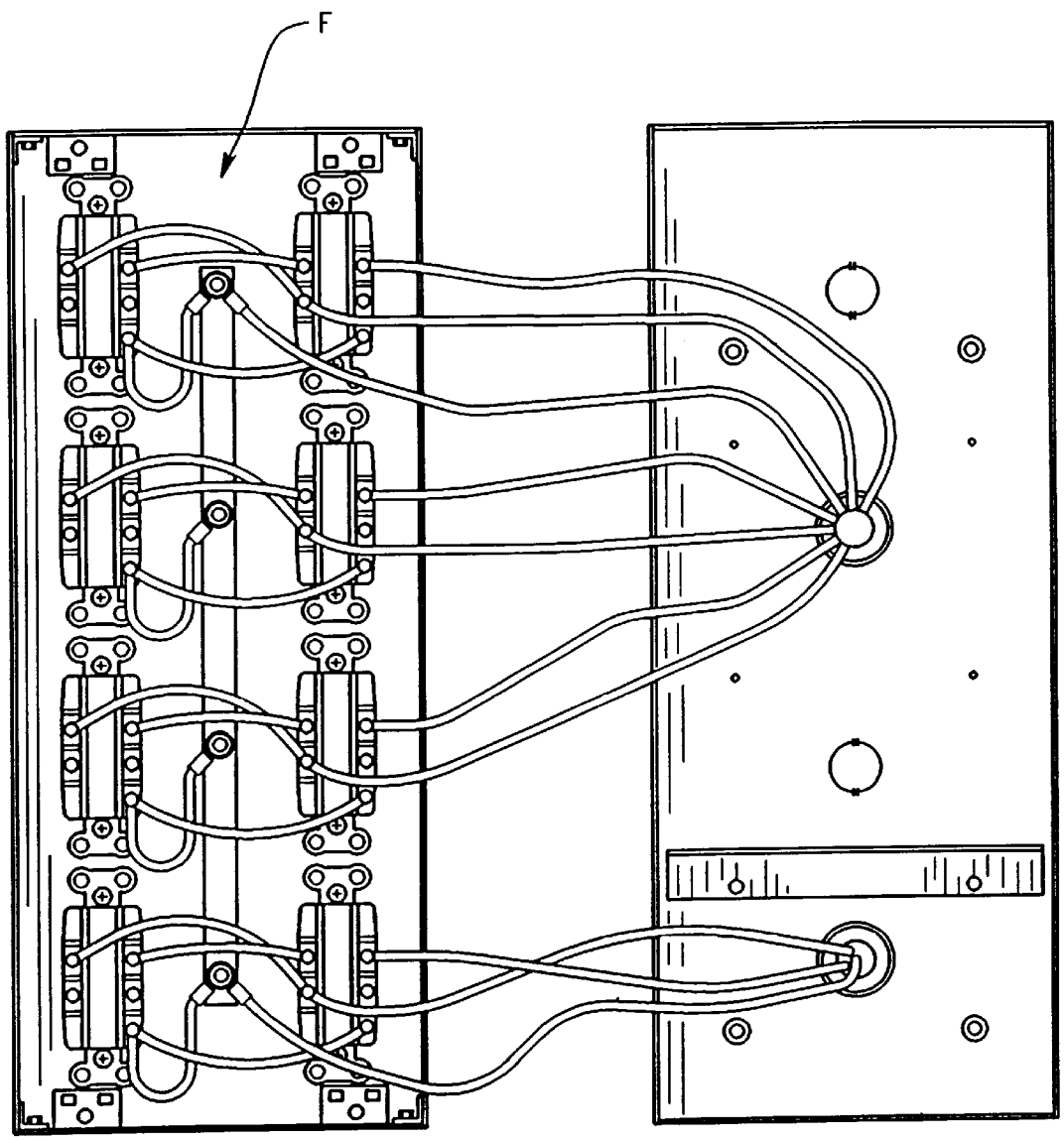
FIG. 3 is an elevational view of the left electrical connection box of FIG. 2 in an opened position illustrating the various electrical outlet connections within the box.
Figure 4:
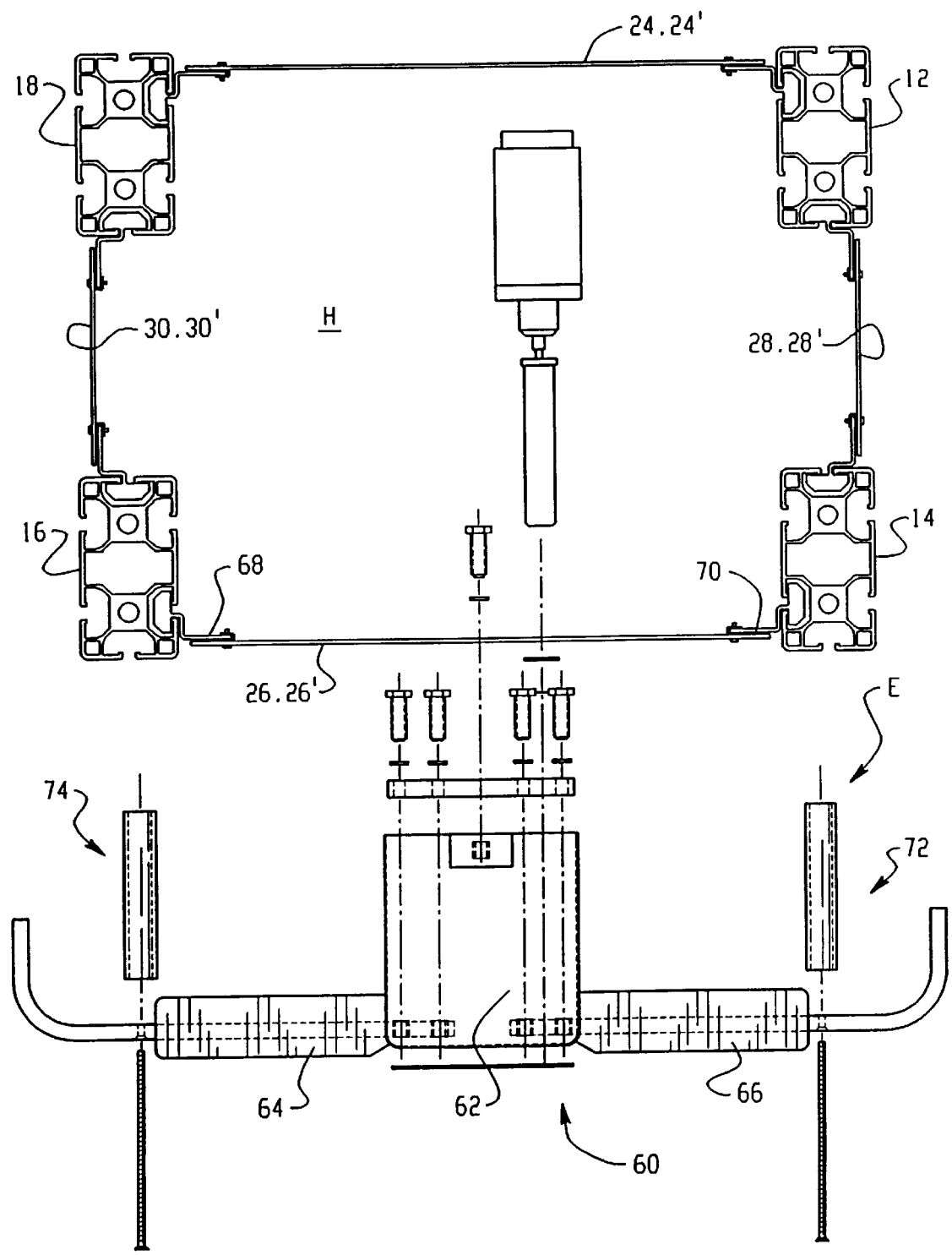
FIG. 4 is a view of the subject system in partial cross section and including an exploded view of the manual handle and motor control panel of the system of FIG. 1.

With reference now to the FIGURES, and in particular first to FIGS. 1, 1A, and 2, the preferred embodiment of the subject surgical equipment management system formed in accordance with the present invention includes a substantially rectangular box-shaped main body portion A suspended from overhead by an overhead support apparatus B, B'. FIG. 1 shows the main body portion A supported by a single rotatable horizontal arm. Alternatively, the main body portion could be supported by multiple movable (rotatable) and motorized arm segments as shown in FIG. 1A.

Preferably, the single rotatable support arm mechanism shown in FIG. 1 permits rotation of the entire system as shown generally by the arrow. The rotatable joint is lockable in place using pneumatic brakes, or the like, as is well known in the art. In the drawing of FIG. 1A, the multiple arm support mechanism permits rotation of the arm segments as shown generally by the circular arrows. Further, the multiple arm support mechanism is preferably motorized at the lower joint to enable pivotal vertical motion to adjust the height of the main body portion as shown generally by the curved vertically oriented arrow. Each of the rotatable joints are lockable in place using pneumatic brakes or the like.

The overhead support apparatus B is directly connected to suitable structural reinforcement members in the ceiling of an operating room or the like. A large horizontal support table C extends forward from the face of the vertical main body column to form a main platform for supporting medical apparatus or to engage hooks or other mounting devices on the top or sides of a medical apparatus.

Multiple gas connections D are provided on the rear face of the main body portion on a side opposite the main platform. The connections deliver gas to patients during surgical procedures and supply power to medical devices. A manual handle E is included below the gas connections near the bottom of the rear face of the main body column as shown. The manual handle provides a convenient point to grip and move the body column into place within the operating room as desired. A set of electrical connections F are provided on the left face of the body column and optional shelves G (FIG. 8A) are selectively attached below the main platform on the front face of the body column.

As best shown in FIG. 1, the manual handle includes a set of manually actuatable pushbuttons I for controlling the pneumatic brakes and a manually actuatable toggle switch J for controlling the motorized vertical height adjusting motion of the main body portion. In the single arm overhead support system shown in FIG. 1, only one of the pushbuttons is used because the system includes only a single pneumatic brake in the single overhead rotatable arm joint. In the double arm overhead support system shown in FIG. 1A, both brake pushbuttons are used to each respectively control one of the pneumatic brakes in the rotatable arm joints. The toggle switch J is operational as well to control the motorized vertical height adjustment of the main body column. As is well known in the art, the pneumatic brakes release when the pushbuttons are depressed. The toggle switch is preferably a spring return to center type so that vertical motion is enabled only when an operator presses and holds the switch in a downward or upward position.

Turning next to a more detailed discussion of the individual components and construction of the subject surgical equipment management system, reference will be made to the mechanical drawings provided in FIGS. 1–11. Overall, the vertical main body column 10 is formed by four individual ribbed aluminum extrusion members 12, 14, 16, and 18 connected together at their top and bottom ends by a corresponding top closure member 20 and a bottom closure member 22. The four individual ribbed extrusion members and related connecting hardware used in the assembly of the instant surgical equipment management system design are each separately commercially available and well known in the art. A set of four vertical face panels 24, 26, 28, and 30 interconnect with the ribbed extrusion members to form a very rigid vertical rectangular box-shaped main column 10. The main body column is substantially hollow forming an internal channel H adapted to carry the routing of electrical and gas connections, hoses, wiring, and the like.

Figure 5:
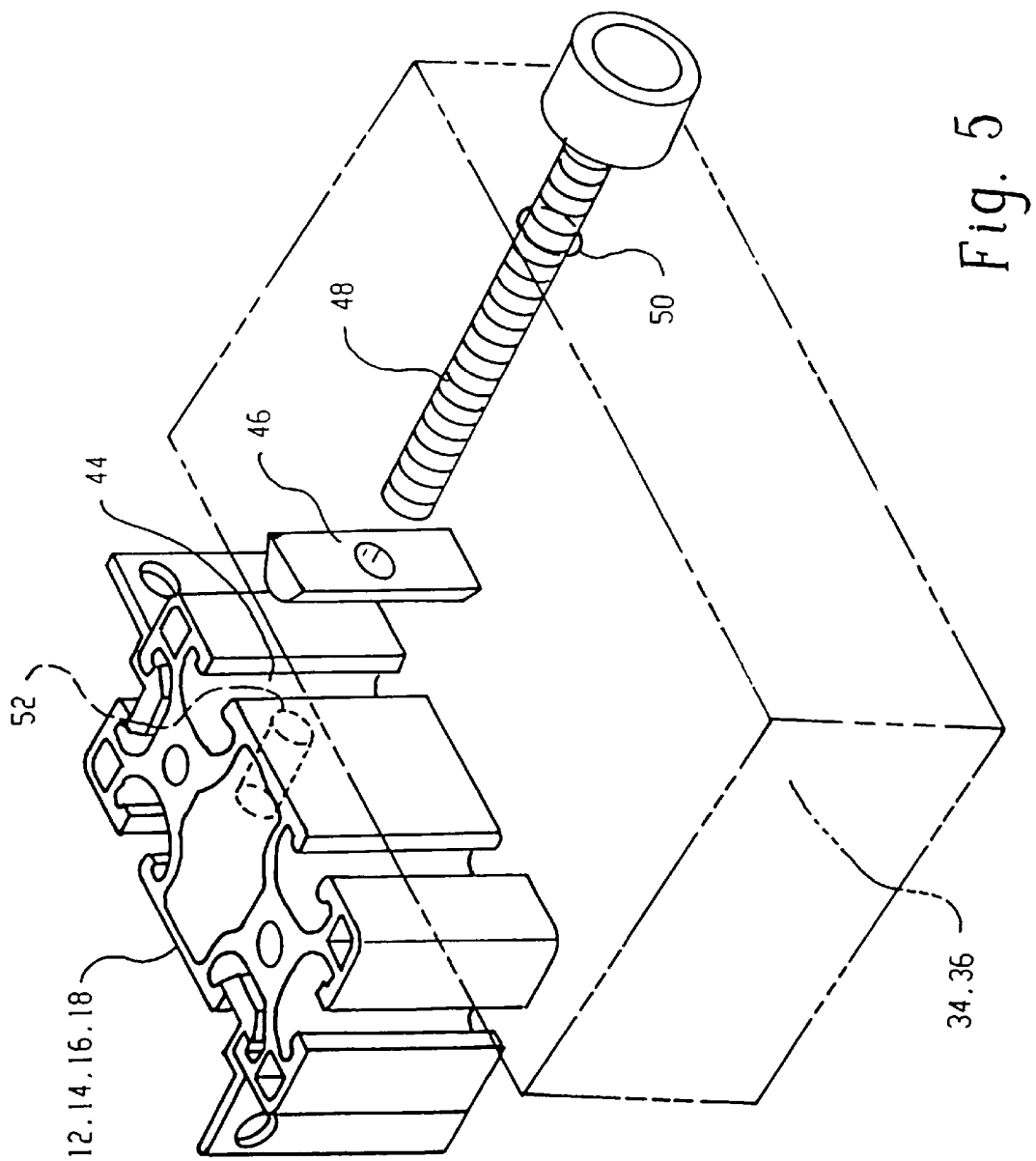
FIGS. 5, 6A and 6B illustrate alternative preferred embodiments of the safety bolt and captive nut mounting arrangement used to attach various platforms and the like to the surgical equipment management system of the present invention.
Figure 6A:
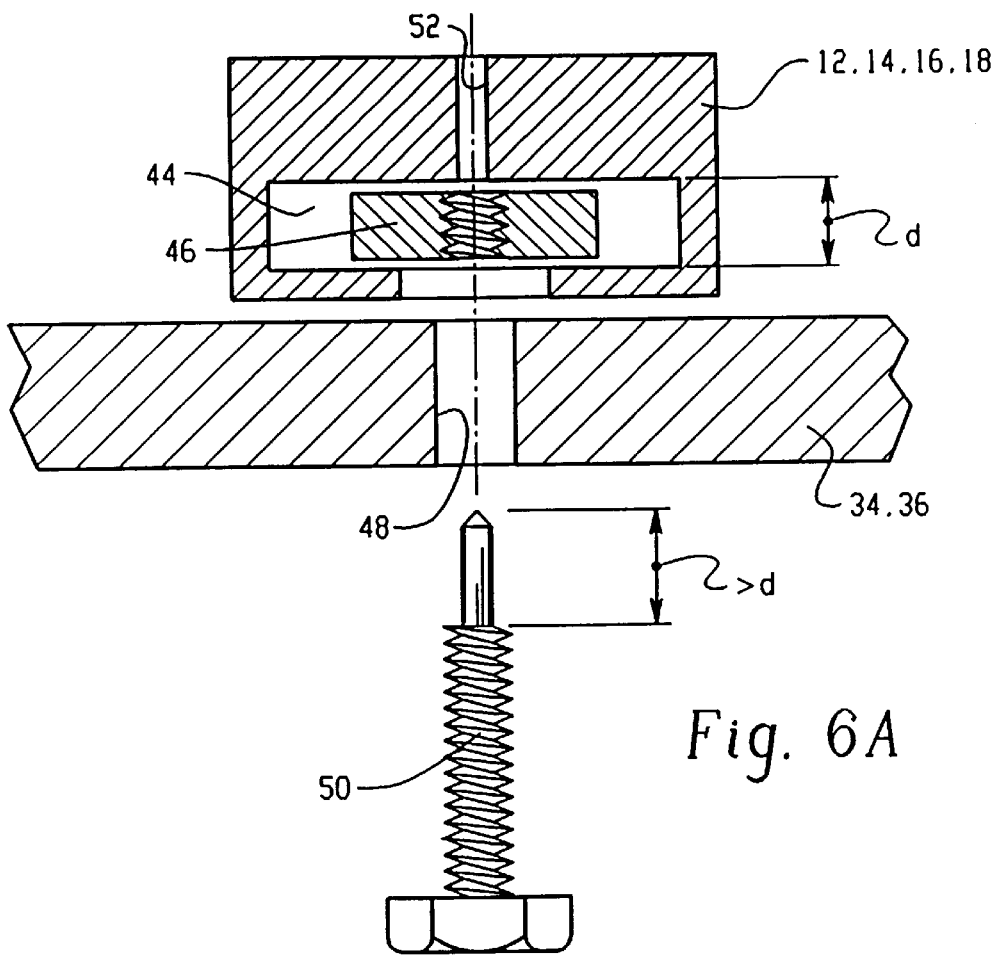

As best shown in FIG. 2, the main platform 32 of the subject appliance support system includes a pair of horizontally disposed ribbed extension members 34, 36 connected on one end to the main body column and supporting a planar shelf member 38 on their outer, free ends. The first extension member is connected to the left pair of extrusion members 12, 14 and the second extension member is connected to the right pair of extrusion members 16, 18. The pair of horizontal extension members are preferably formed substantially identically in cross section to the vertical extrusion members 12, 14, 16 and 18 at the four edges of the main body column. In that regard, the horizontal extension members 34, 36 are preferably provided with elongate indentations 44 such as shown in FIGS. 5 and 6. The indentations form slots that are adapted to receive slide nuts therein. The slide nuts in the horizontal extrusion members are engaged with suitable cooperative bolts extending through countersunk holes provided in the planar shelf member 38. In that manner, by simply loosening the bolts, the main platform can be moved horizontally towards and away from the main support column. Conversely, tightening the bolts locks the main platform into place horizontally.

Vertical adjustment of the main platform 32 relative to the main body column 10 is not possible, however, due primarily to the oversized safety bolts 50 used to attach the platform to the main body column. Each of the safety bolts extend completely through the horizontal extension members 34, 36 and into one of the vertical members 12, 18, locking the main platform in place. This arrangement provides an added measure of safety to the equipment support system of the invention in that the shelf is thus prevented from loosening and falling from the main column.

In addition to the above, upward movement of the main platform is blocked as well by the left and right side electrical connection boxes 40, 42 attached to the main body column 10 as illustrated. As shown best in FIG. 2, the vertical dimension of the corner extrusion members forming the main body column precludes the possibility of useful practical downward movement of the platform.

In accordance with an aspect of the invention, a set of relief bores 52 are formed at selected locations to cooperate with the lead ends of the safety bolts 50. The length of the safety bolts used to connect the main platform to the main body column are carefully sized to include an excessive length portion extending into the corresponding set of safety lock relief bores 52 provided in the corner extrusion members. More particularly, the connection of the main platform 32 to the corner extrusion members 12–18 can best be described with reference to the schematic drawings at FIGS. 5 and 6.

Figure 6B:
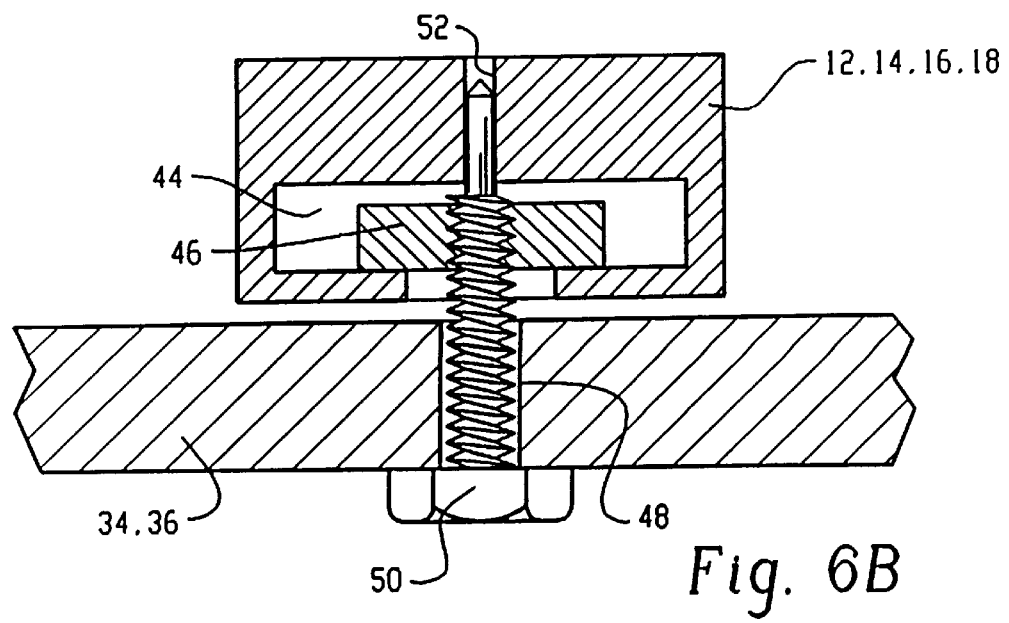
Figures 7A, 7B:
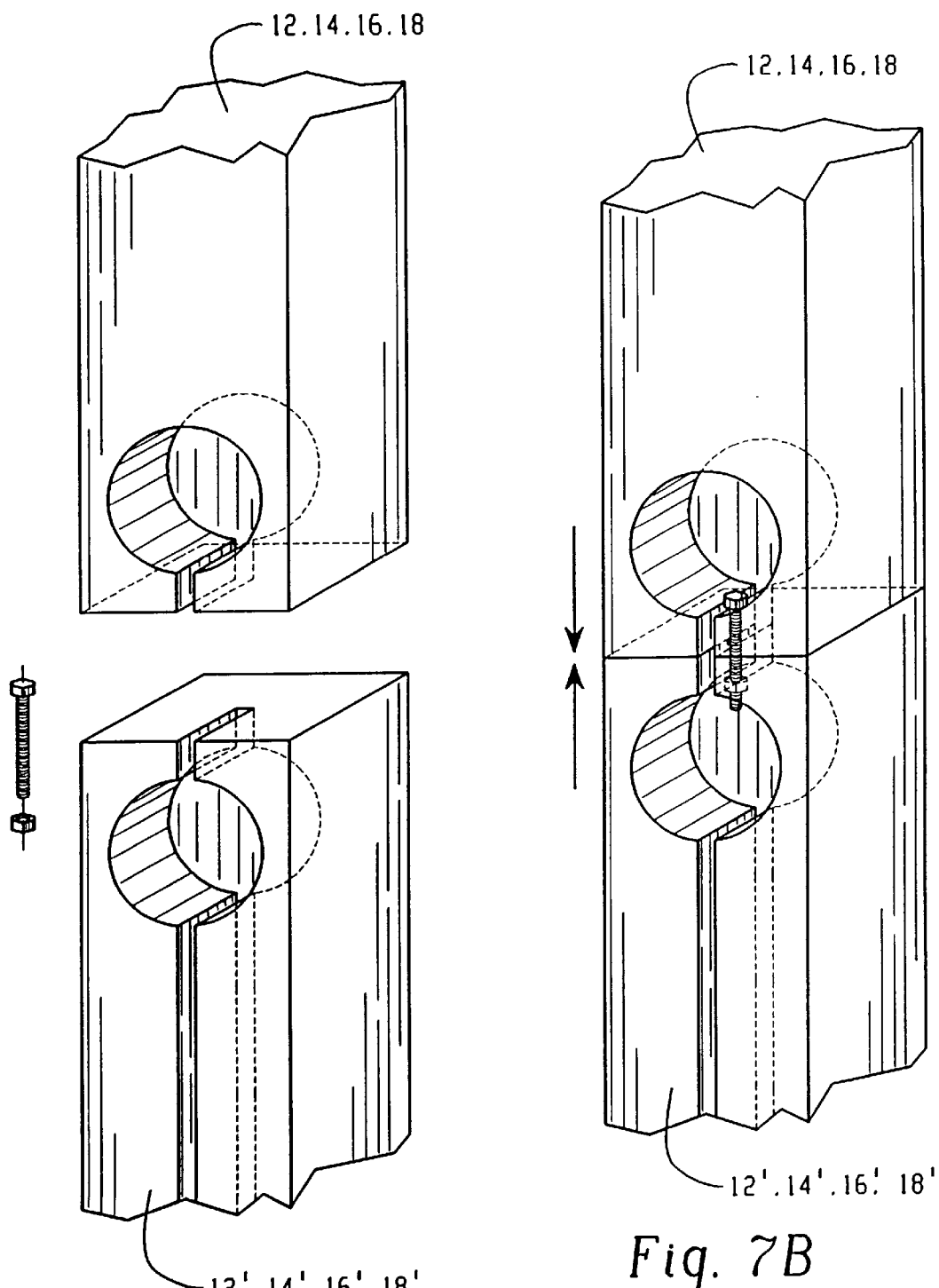
FIGS. 7A and 7B are schematic illustrations of the preferred butt splice connection used for extending the main body column of the subject system to provide for optional auxiliary shelves below the main platform.

Turning now to those Figures, each of the ribbed corner extrusion members 12–18 forming the corners of the main body column include elongate grooves or indentations 44 adapted to snap-receive a set of internally threaded captive nuts 46. Suitable clearance fit holes 48 are provided through the horizontal extension members 34, 36 of the main platform to receive the threaded safety bolts 50 therethrough. The safety bolts threadedly engage the captive nuts 46 disposed in the elongate indentations 44 of the vertical corner extrusion members 12–18 as shown in FIG. 6B. However, because of their excessive length, as the bolts are tightened, the lead end of each bolt enters into a support recess 52 before the enlarged head end of the bolt clamps the horizontal extrusion members to the main body column. The support recesses are provided in the corner extrusion members 12–18 at suitable locations so as to correspond spatially with the clearance fit holes 48 formed in the horizontal extrusion members. In that regard, as an added measure of safety, the bolts are adapted to provide vertical support for the horizontal extrusion members of the main platform without any clamping action being performed by the captive nuts 46 within the elongate indentations 44.

The primary purpose and function of the captive nuts 46 is to assist in stabilizing the mechanical connection between the horizontal extrusion members and the corner extrusion members on the main body column. The support recesses are carefully formed in the vertical extrusion members so as to provide adequate clearance for the lead end of each safety bolt so that the bolts can be advanced therein until the enlarged head end of the bolts engage the horizontal extrusion members of the main platform. After the bolts are tightly clamped to the captive nuts, the support recesses 52 provide a backup safety "catch" to the main platform so that, in the unlikely and unfortunate event that any of the safety bolts or captive nuts loosen, the loose connection will continue to provide adequate support for the main platform by the engagement of the lead end of the safety bolt with the corresponding support recess.

As indicated above, the main body column 10 of the surgical equipment management system supports a left and right side electrical connection box 40, 42, respectively. Each of the side boxes are mounted to the set of ribbed extrusion members 12–18 in a manner substantially identical to the main platform system described above. More particularly, each of the side boxes 40, 42 are attached to the ribbed extrusion members using elongate safety bolts connected to captive nuts disposed in elongate grooves or indentations formed in the ribbed extrusion members. In addition, each of the safety bolts are selected to have an excessive length portion so that the lead ends thereof engage corresponding support recesses formed in the ribbed extrusion members. In that way, the side boxes are vertically immovable on the main body column.

In addition, a margin of safety is provided to the side boxes because of the use of the elongate safety bolt and support recess connection strategy described above. In the unlikely and unfortunate event that any of the safety bolt and captive nuts loosen, the engagement of the lead end of the safety bolts within the support recesses ensures that the side boxes will not move vertically along the main body column under any condition.

As briefly described above, a manual handle member 60 is provided at the rear face of the main body column opposite the main platform to enable a circulating nurse or other surgical assistant to move the surgical equipment management system apparatus of the instant invention into and out of the surgical field, toward or away from the operating table or into any other position as desired. The rear handle mechanism 60 includes a central base member 62 and a pair of outwardly extending manual grip members 64, 66. The central base member 62 is connected directly to the rear face panel 26 using suitable bolts and washers as illustrated. More particularly, the central base member 62 includes a plurality of internally threaded holes adapted to receive a corresponding plurality of cap screws which extend through clearance holes provided in the rear face panel 26. The rear face panel 26 is, in turn, connected to the corresponding vertical extrusion members 14, 16 using a pair of elongate captive nuts 68, 70 held in place within the indentations using suitable set screws or the like. The elongate captive nuts 68, 70 extend substantially the entire length of the elongate indentations provided in the ribbed extrusion members. Thus, the elongate captive nuts, as well as the rear face panel 26, the central base member 62, and the grip members 64, 66 connected thereto, are prevented from moving vertically relative to the main body column.

In order to provide mechanical support to the grip members 64, 66 against forces in a horizontal direction as the grip members are tugged and pushed to position the subject surgical equipment support system into place, a pair of fastener sets 72, 74 are provided as illustrated. The fastener sets include an elongate threaded bolt extending through countersunk holes provided in the grip members and captive nuts snap-fitted into the elongate indentations formed in the vertical ribbed extrusion members. Hollow spacer members limit the horizontal deflection of the grip members as the subject surgical equipment support system is manually positioned into place during use. A set of metallic cover strips are provided preferably disposed within the elongate grooves above and below the captive nuts for both cosmetic and mechanical reasons. The cover strips fill the vertically extending gaps created by the elongate indentations in the ribbed extrusion members. In addition, the cover strips prevent vertical movement of the fastener sets 72, 74 within the elongate grooves or indentations.

As noted above, the surgical equipment management system of the present invention is readily adaptable to include optional additional shelves G held below the main platform in an "extended head" configuration. In that regard, the extended head embodiment includes a set of ribbed extension members 12'–18' which are butt splice connected (FIG. 7) to the vertical ribbed extrusion members 12–18 arranged in the four corners of the main body column 10. Suitably sized auxiliary face panels 24'–30' are disposed between the set of ribbed extension members 12'–18' to provide for an extended inner supply channel in the main body column.

Figure 8A:
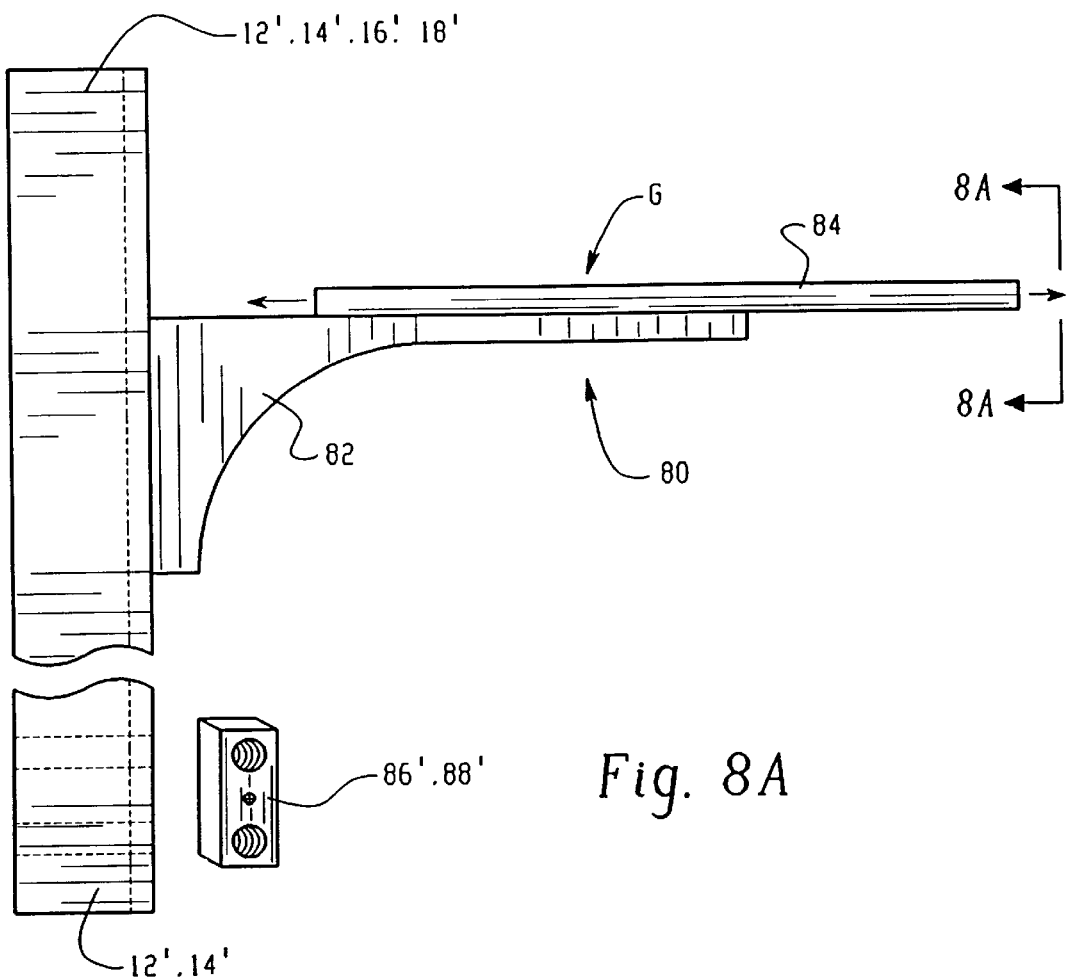
FIGS. 8A and 8B illustrate the manner in which auxiliary appliance support shelves are attached to the vertical head extension shown in FIGS. 7A and 7B; and, FIGS. 9 and 9A–9C illustrate the method and components used to mount the front, back and side panels forming the main body portion of the support column; and, FIGS. 10 and 11 illustrate an elongate captive nut member and a panel connection to the column body corner extrusion support member using the elongate captive nut member.
Figure 8B:
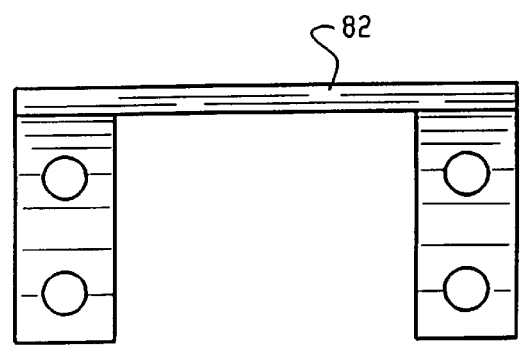
Figure 9:
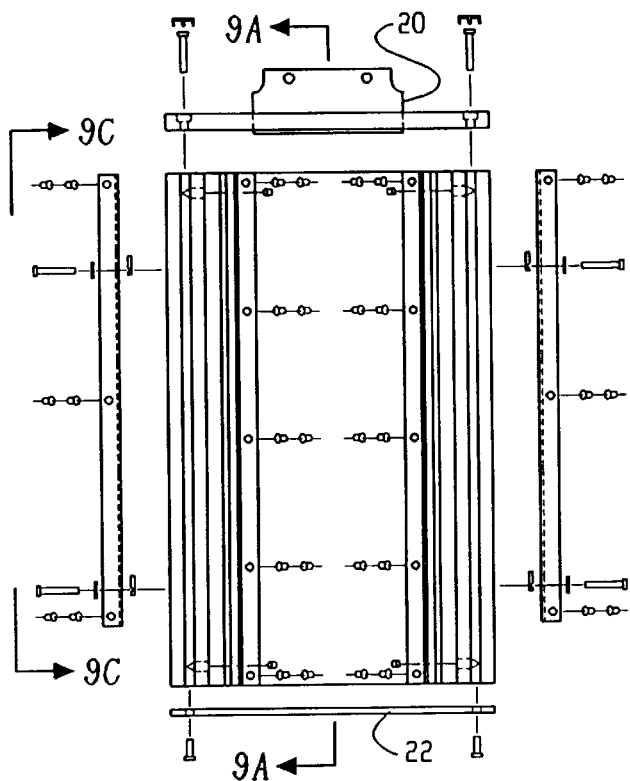
Figure 9A:
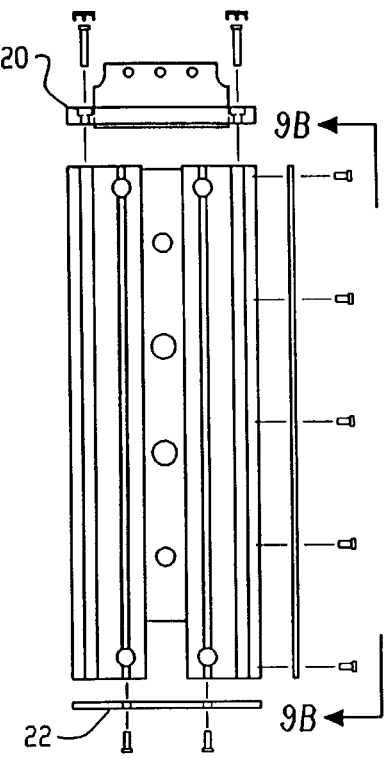
Figure 9C:
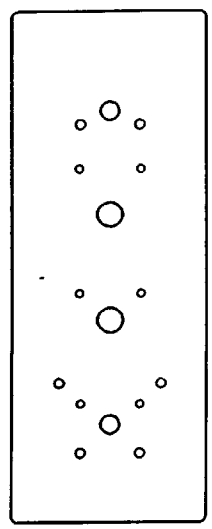
Figure 9B:
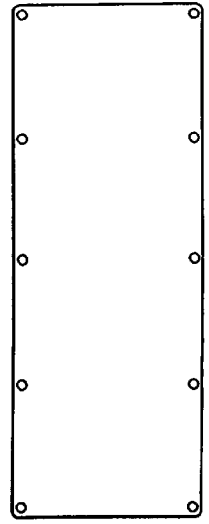

FIGS. 8A and 8B illustrate an auxiliary shelf 80 which includes a shelf bracket 82 supporting a planar shelf member 84 thereon. The shelf bracket 82 includes a set of four clearance holes adapted to accept a corresponding set of safety bolts of the type described above. The bolts are adapted to engage a pair of dual captive nuts 86, 88 snap-fit into the elongate indentations provided in the auxiliary extension members 12', 14'. The dual captive nuts 86, 88 are each provided with a pair of internally threaded holes adapted to receive a corresponding pair of safety bolts therethrough. In a manner as described above, the ribbed extension members 12', 14' are each provided with a set of support recesses disposed at predetermined locations and adapted to accommodate the lead ends of the safety bolts.

The auxiliary shelf 80 is attached to the main body column extension in a manner substantially identical to the connection between the main platform 32 and the main body column. More particularly, the auxiliary shelf 80 is vertically immovable on the main body column extension due primarily to the mechanical interface between the lead ends of the safety bolts with the support recesses provided in the ribbed extension members.

The invention has been described with reference to the preferred embodiments. Obviously, modifications and alterations will occur to others upon a reading and understanding the preceding detailed description. It is intended that the invention be construed as including all such modifications and alterations insofar as they come within the scope of the appended claims or the equivalents.

Having thus described the preferred embodiment, the invention is now claimed to be:

1. A convertible medical appliance support apparatus comprising:

a top substantially rectangular closure member adapted to connect the support apparatus to an operatively associated ceiling mount member;

a bottom substantially rectangular closure member;

a first pair of elongate corner support members extending substantially vertically between the top closure member and the bottom closure member;

a second pair of elongate corner support members extending substantially vertically between the top closure member and the bottom closure member;

a first pair of face wall members, a first one of the first pair of face wall members connecting the first pair of corner support members and a second one of the first pair of face wall members connecting the second pair of corner support members;

a first pair of side wall members, a first one of the first pair of side wall members connecting a first one of the first pair of corner support members with a first one of the second pair of corner support members, and a second one of the first pair of side wall members connecting the second one of the first pair of corner support members with the second one of the second pair of corner support members;

a medical appliance support member connected to at least one of the first and second pair of elongate corner support members and adapted to support an operatively associated medical appliance on the convertible medical appliance support apparatus;

an extension system including i) a first pair of elongate corner support extension members having a free end and a connection end, the connection end of the first pair of extension members being selectively connectable to said first pair of elongate corner support members for extending the medical appliance support apparatus in a direction beyond the bottom closure member, and ii) a second pair of elongate corner support extension members having a free end and a connection end, the connection end of the second pair of extension members being selectively connectable to said second pair of elongate corner support members for extending the medical appliance support apparatus in said direction beyond the bottom closure member;

the bottom substantially rectangular closure member being selectively connectable to the free end of the first pair of corner support extension members and to the free end of the second pair of corner support extension members;

the first one of the first pair of face wall members being adapted to connect the first pair of corner support extension members, and the second one of the first pair of face wall members being adapted to connect the second pair of corner support extension members; and, the first one of the first pair of side wall members being adapted to connect a first one of the first pair of corner support extension members with a first one of the second pair of corner support extension members, and the second one of the first pair of side wall members being adapted to connect the second one of the first pair of corner support extension members with the second one of the second pair of corner support extension members.

2. The medical appliance support apparatus according to claim 1 wherein:

the top closure member, the bottom closure member, and the first pair of face wall members are adapted for replacement with a second top closure member, a second bottom closure member, and a second pair of face wall members, respectively, to modify a width dimension of said main body portion.

3. The medical appliance support apparatus according to claim 1 wherein:

the top closure member, the bottom closure member, and the first pair of side wall members are adapted for replacement with a second top closure member, a second bottom closure member, and a second pair of side wall members, respectively, to modify a depth dimension of said main body portion.

4. The medical appliance support apparatus according to claim 1 wherein:

the top closure member, the bottom closure member, the first pair of face wall members, and the first pair of side wall members are adapted for replacement with a second top closure member, a second bottom closure member, a second pair of face wall members, and a second pair of side wall members, respectively, to modify both a width and depth dimension of said main body portion.

5. The medical appliance support apparatus according to claim 1 wherein said medical appliance support member is selectively connectable to said first pair of elongate corner support members and includes a substantially planar shelf member disposed adjacent a first one of said first pair of face wall members.

6. The medical appliance support apparatus according to claim 5 further comprising:

a manual handle adapted to interface the medical appliance support apparatus with a human operator for movement of the medical appliance support apparatus relative to a fixed end of said operatively associated ceiling mount member, the manual handle being disposed adjacent the second one of said first pair of face wall members so that said medical appliance support member and the manual handle are disposed on opposite sides of said main body portion.

7. The medical appliance support apparatus according to claim 6 wherein said second one of said first pair of face wall members includes a plurality of gas outlet connections, the plurality of gas outlet connections including at least three rows and three columns of gas outlet connections.

8. The medical appliance support apparatus according to claim 7 wherein said plurality of gas connections include at least one redundant gas connection.

9. The medical appliance support apparatus according to claim 5 wherein said extension system is adapted to carry said planar shelf member relative to the first pair of elongate corner support members.

10. A medical appliance support apparatus comprising:

a box-shaped main body portion defining a columnar space for suspension in a room using an external associated overhead support device;

at least one substantially planar shelf member extending from a front face surface of the box-shaped main body portion of the medical appliance support apparatus, the shelf member being adapted to support an associated medical appliance relative to the room;

a manual handle member disposed on a rear face surface of the main body portion on a side of the medical appliance support apparatus opposite from said substantially planar shelf member, the handle member being adapted for grasping by hand to move the main body portion into selected multiple positions relative to the room;

at least one manually actuatable input member adjacent said rear face member, the input member being operable for actuating the associated external overhead support device to enable selective locking and releasing of movement of the main body portion relative to the room;

a first pair of face wall members disposed in a parallel relative relationship;

a second pair of face wall members disposed in a parallel relative relationship and generally perpendicular to said first pair of face wall members; and, a set of elongate corner connection members adapted to selectively engage edges of the first and second pair of face wall members and hold them in a relative spaced apart relationship to define said columnar space therebetween, the set of corner connection members and the first and second pair of face wall members being adapted to enable selective replacement of at least one of the first pair of face wall members and the second pair of face wall members with a replacement pair of face wall members to change the size of said columnar space.

11. The medical appliance support apparatus according to claim 10 wherein the set of corner connection members and the first and second pair of face wall members are adapted to enable selective replacement of both the first and second pair of face wall members with a respective first and second set of replacement pair of face wall members to change the size of the columnar space in both a width dimension and a depth dimension.

12. The medical appliance support apparatus according to claim 10 further including a set of elongate corner connection extension members adapted to selectively engage said set of corner connection members and said edges of the first and second pair of face wall members to modify said size of the columnar space in a height dimension.

* * * * *